United States Patent [19]
Takeuchi et al.

[11] Patent Number: 6,048,820
[45] Date of Patent: Apr. 11, 2000

[54] COPPER-BASED CATALYST AND METHOD FOR PRODUCTION THEREOF

[75] Inventors: Masami Takeuchi; Hirotaka Mabuse; Taiki Watanabe; Michiaki Umeno; Takashi Matsuda; Kozo Mori; Kenji Ushikoshi; Jamil Toyir; Shengcheng Luo; Jingang Wu, all of Tokyo; Masahiro Saito, Tsukuba, all of Japan

[73] Assignees: Agency of Industrial of Sciences and Technology, Tokyo; The Reseach Institute of Innovative Technology for the Earth, Kyoto, both of Japan

[21] Appl. No.: 09/037,011

[22] Filed: Mar. 9, 1998

[30] Foreign Application Priority Data

Mar. 11, 1997 [JP] Japan .................................. 9-055912
Oct. 27, 1997 [JP] Japan .................................. 9-294097

[51] Int. Cl.$^7$ .............................. B01J 21/08; B01J 21/12; B01J 21/14; B01J 23/72
[52] U.S. Cl. .......................... 502/244; 502/250; 502/345; 502/346; 502/342; 502/343
[58] Field of Search .............................. 502/238, 243, 502/244, 250, 345, 346, 342, 343

[56] References Cited

U.S. PATENT DOCUMENTS 4,199,479 4/1980 Wilkes ...................... 252/457

5,767,039 6/1998 Yamagishi et al. ................. 502/342

FOREIGN PATENT DOCUMENTS 60-97048  5/1985  Japan .
63-39287  8/1988  Japan .
27645  1/1989  Japan .
6-254414  9/1994  Japan .

*Primary Examiner*—Richard Booth
*Assistant Examiner*—Alexander G. Ghyka
*Attorney, Agent, or Firm*—Armstrong, Westerman, Hattori, McLeland & Naughton

[57] ABSTRACT

The invention relates to a copper-based catalyst with high activity and a long catalyst life and to a method of producing the catalyst. This catalyst essentially comprises copper oxide, zinc oxide, aluminum oxide, and silicon oxide and optionally containing zirconium oxide, gallium oxide, and palladium oxide, wherein with the total weight of the catalyst being taken as 100%, the above oxides account for, in the order mentioned, 20–60 weight %, 10–50 weight %, 2–10 weight %, 0.3–0.9 weight %, 0–40 weight %, 0–10 weight %, and 0–10 weight %, respectively, and the silicon oxide mentioned above has been derived from colloidal silica or dissolved silica in water, which catalyst has been subjected to calcination at 480–690° C.

3 Claims, 3 Drawing Sheets

ACTIVITY RATIO = METHANOL YIELD AT 1000 HOURS OF REACTION/
METHANOL YIELD AT INITIAL PHASE OF REACTION

COPPER-BASED CATALYST AND METHOD FOR PRODUCTION THEREOF

TECHNICAL FIELD

The present invention relates to a copper-based catalyst possessing a high activity and a remarkably long life for use in methanol synthesis reaction or the reverse reaction thereof and to a method of producing the catalyst.

BACKGROUND OF THE INVENTION

BRIEF DESCRIPTION OF THE PRIOR ART

The process for methanol synthesis from synthesis gas (a mixture gas of CO and $H_2$) containing a small amount of $CO_2$ is a very important basic process in chemical industry and there is a standing need for improving the efficiency of the process from the standpoint of energy savings and other economics. One of the most important technologies in the field of methanol synthesis is that of providing a high performance catalyst, and as such catalysts, several ternary catalysts including the $Cu/ZnO/Al_2O_3$ catalyst (current industrial catalysts) [e.g. Shokubai Koza, Vol. 7, ed. by the Catalyst Society of Japan, Kodansha, Jul. 20, 1989, pp. 21–39] and the $Cu/ZnO/SiO_2$ catalyst (Japanese Kokai Tokkyo Koho No. 39287/1988), among others, are known.

Recently, methanol synthesis from $CO_2$ and $H_2$ as main raw materials has been a focus of attention from the standpoints of recycling of the carbon resources and of conservation of global environment. In the synthesis of methanol from a $CO_2$-rich feed gas, the thermodynamic equilibrium of the reaction and the reaction-inhibitory effect of by-product water accompanying the formation of methanol (Applied Catalysis A: General, 38, 1996, pp. 311–318) require for the use of a catalyst having higher activity than the conventional catalyst used in said methanol synthesis from synthesis gas. Furthermore, in the synthesis of methanol from a $CO_2$-rich feed gas, the deactivation of catalyst which is apparently attributable to the by-product water is remarkably great as compared with said synthesis of methanol from synthesis gas. Therefore, a demand exists for a catalyst with a much longer catalyst life than the catalyst used in the methanol synthesis from synthesis gas. This is because the ternary catalysts used conventionally for methanol synthesis from synthesis gas are insufficient in catalyst performance for methanol synthesis from a $CO_2$-rich feed gas.

In view of the above circumstances, some of the inventors of the present invention previously developed several copper-based multi-component catalysts including a copper/zinc oxide/aluminum oxide/zirconium oxide catalyst and a copper/zinc oxide/aluminum oxide/zirconium oxide/gallium oxide catalyst, among others (e.g. Japanese Kokai Tokkyo Koho No. 39755/1995, Japanese Kokai Tokkyo Koho No. 312138/1994, Applied Catalysis A: General, 38 (1996), pp. 311–318). The present invention represents a further breakthrough in the art including of those prior inventions. In the field of technology relating to copper-based multicomponent catalysts to which the present invention belongs, the following patent applications are known.

(1) Japanese Kokai Tokkyo Koho No. 254414/1994 discloses a method for producing a methanol synthesis catalyst from precursors of copper oxide and zinc oxide and a precursor of zirconium oxide or/and of aluminum oxide and containing 1–30 weight % of $CO_2$ equivalent. The salient feature of the invention described in this official publication resides in the use of a catalyst precursor formulation containing a suitable amount of a $CO_2$ source while the per se known basal composition for a methanol synthesis catalyst is retained. When a carbonate or a hydrogen carbonate is used as the precipitant in the step of precipitating copper and zinc components from an aqueous solution containing a water-soluble copper salt and a water-soluble zinc salt, the very precipitant serves as a $CO_2$ source but when the precipitant does not contain carbonic acid, a calculated amount of $CO_2$ gas must be blown into the catalyst formulation. It is stated in the above publication that where necessary one or more precursor components selected from among oxy acids of silicon, boron, chromium, vanadium, magnesium, and phosphorus, inclusive of salts thereof, may be added but only the use of boric acid is displayed in the examples. Regarding the calcination temperature, there is no particular description but there are references to the drying operation performed at 280° C., 200° C., and 300° C. in the working examples and at 400° C., 220° C., and 300° C. in the comparative examples. The temperature for reduction of catalyst precursors is said to be 100–300° C., preferably 120–200° C. As to the starting gas composition for use in methanol synthesis, only the case of using a gas of the composition $H_2$ 67.4%, CO 24.0%, $CO_2$ 6.6%, $CH_4$ 1.5%, and $N_2$ 0.5% is shown. This publication does not contain an example of methanol synthesis from a $CO_2$-rich synthesis gas and no information is available on catalyst activity and life.

(2) Japanese Kokai Tokkyo Koho No. 27645/1989 discloses a catalyst suitable for carbon oxide conversion (shift reaction and methanol synthesis) which comprises copper metal and zinc oxide and/or magnesium oxide and the metallic copper component of which has a surface area of at least 70 $m^2$ per gram copper. It is mentioned that this catalyst may optionally contain the element X selected from among Al, V, Cr, Ti, Zr, Tl, U, Mo, W, Mn, Si, and rare earth metals in a proportion of 2–50%, particularly 4–30%, relative to the total amount of Cu, Zn, Mg, and X. In the examples, only the use of Al in combination with Zn is shown for X. As to calcination temperature, it is stated that calcination is carried out at a temperature over 250° C. and generally at a temperature within the range of 300–350° C. Regarding the temperature for the reduction to metallic copper, it is mentioned that the reduction is carried out at a selected temperature not exceeding 250° C. and preferably not higher than 200° C. With regard to the starting gas composition, only the composition $H_2O$ 33.3 vol. %, $N_2$ 14.8 vol. %, $CO_2$ 6.1 vol. %, CO 5.7 vol. %, $H_2$ 33.3 vol. % is used in the examples. This official publication does not contain an example concerning the synthesis of methanol from a $CO_2$-rich gas, either, and no information is available on catalyst activity and life.

(3) Japanese Kokai Tokkyo Koho No. 32949/1984 referred to above (Japanese Patent Publication No. 39287/1988) discloses a methanol synthesis catalyst comprising copper oxide, zinc oxide, and silicon oxide. The atomic ratio to metals of silicon is 0.05–10%, preferably 0.1–3.5%. As to the silicon component, it is mentioned that any of silicon oxide sol, hydrogel, xerogel, and aerogel can be used as the starting material, with the hydrogel providing a particularly remarkable effect, that said hydrogel can be prepared typically by adding alkali to an acidic solution of a water-soluble silicate, and that the silicate may for example be sodium silicate or potassium silicate, with sodium silicate being particularly preferred. In the examples, an aqueous solution of sodium silicate (Examples 1, 3, 4), silica hydrogel (Example 2), silica xerogel (Example 5), and silica aerosol (Example 6) are used. It is stated that calcination can be carried out in an oxygen-containing atmosphere at a temperature of at least 300° C., preferably 330–400° C. (370° C. in the examples). However, the catalyst disclosed in this official publication is limited to the Cu/Zn/Si ternary oxide catalyst and, as to the composition of the starting gas for methanol synthesis, only the use of a gas of the composition $H_2$ 70%, CO 23%, $CO_2$ 3%, $CH_4$ 3.5%, $N_2$ 0.5% is mentioned.

(4) Japanese Kokai Tokkyo Koho No.97048/1985 discloses a catalyst for use in the synthesis of fuel alcohol, which comprises copper oxide, zinc oxide, an oxyacid salt of phosphorus and/or silicon oxide, and at least one compound selected from among potassium, rubidium, and cesium. The Cu/Zn ratio is 0.2–3, and the Si/Zn ratio is 0.001–0.07, preferably 0.005–0.05. As the silicon component, it is stated that any of silicon oxide sol, hydrogel, xerogel, and aerosol can be used as a raw material, with the hydrogel providing a particularly beneficial effect, that said hydrogel can be prepared typically by adding alkali to an acidic solution of a water-soluble silicate, and that said silicate may for example be sodium silicate or potassium silicate, with sodium silicate being particularly preferred. In the examples, a silica hydrogel slurry (Example 2) or a silica hydrogel (Example 6) is used. It is also stated that calcination can be carried out in an oxygen-containing atmosphere at a temperature of at least 300° C., preferably 330–400° C. With regard to the starting gas composition, the composition CO 22.8%, $CO_2$ 6.5%, $CH_4$ 1.5%, $N_2$ 1.2%, $H_2$ 68.0%, the composition $N_2$ 1.6%, CO 31.7%, $CH_4$ 2.6%, $CO_2$ 9.3%, $H_2$ 54.8%, and the composition $N_2$ 0.8%, CO 21.8%, $CH_4$ 1.5%, $CO_2$ 6.1%, $H_2$ 69.8% are shown in the examples.

As mentioned above, the state of the art still requires a high performance catalyst which must possess high activity and a long life for the synthesis of methanol from a $CO_2$-rich gas.

When a gas composed predominantly of $CO_2$ is reacted with $H_2$ on a catalyst to synthesize methanol, the thermodynamic equilibrium of the reaction demands that the reaction be carried out at a lower temperature than said methanol synthesis starting with synthesis gas. Therefore, as pointed out hereinbefore, the catalyst for use must have higher activity than the activity of the catalyst used in the synthesis of methanol from synthesis gas.

Meanwhile, regardless of whether methanol is synthesized from a $CO_2$-rich, CO-lean feed gas or, as practiced today, from a $CO_2$-lean, CO-rich feed gas, the catalyst is deactivated to reduce its productivity for methanol as the reaction is continued for a long time. In order to sustain the productivity for metahnol, therefore, it has been attempted to use a large-sized reactor, to increase the reaction temperature, or to perform a periodic catalyst exchange at a higher frequency but such measures result in a considerable waste of energy and a substantial addition to production cost.

Therefore, a catalyst possessing a higher activity and a longer life is required but, as mentioned above, there has not been developed such a high-activity, long-life catalyst.

It is indeed a goal that must be reached in a very near future to find industrial catalysts that would contribute to the recycling and reutilization of carbon resources and, at the same time, be ecofriendly. The inventors of the present invention did intensive investigations to develop industrially useful high-activity, long-life catalysts for contributing to the protection of the earth's ecology and have developed the present invention.

The present invention, developed under those circumstances, has for its object to provide a copper-based catalyst possessing a high activity and a long life and a method of producing the catalyst.

SUMMARY OF THE INVENTION

The copper-based catalyst according to the present invention is a catalyst essentially comprising copper oxide, zinc oxide, aluminum oxide, and silicon oxide, optionally together with zirconium oxide, gallium oxide, and palladium oxide, wherein with the total weight of the catalyst being taken as 100%, said oxides account for, in the order mentioned, 20–60 weight %, 10–50 weight %, 2–10 weight %, 0.3–0.9 weight %, 0–40 weight %, 0–10 weight %, and 0–10 weight %, respectively, and said silicon oxide has been derived from colloidal silica or dissolved silica in water, which catalyst has been subjected to calcination at 480–690° C.

The production method of the present invention is a method for producing a catalyst essentially composed of copper oxide, zinc oxide, aluminum oxide, and silicon oxide, optionally together with zirconium oxide, gallium oxide, and palladium oxide, wherein with the total weight of the catalyst being taken as 100%, said oxides account for, in the order mentioned, 20–60 weight %, 10–50 weight %, 2–10 weight %, 0.3–0.9 weight %, 0–40 weight %, 0–10 weight %, and 0–10 weight %, respectively, which comprises mixing a solution A, which is an aqueous solution containing water-soluble salts of said metal components except the silicon component, with a solution B, which is an aqueous solution of a base, to form a precipitate, aging the mixture when necessary, washing the precipitate, causing colloidal silica or silica dissolved in water to be adsorbed on the precipitate in the step of said formation, aging, or washing of the precipitate, drying the washed precipitate, and calcining the same at 480–690° C. to provide a calcined catalyst.

DETAILED DESCRIPTION OF THE INVENTION

The present invention is now described in detail.

Catalyst

The copper-based catalyst of the present invention is a catalyst essentially comprising copper oxide, zinc oxide, aluminum oxide, and silicon oxide and optionally containing zirconium oxide, gallium oxide, and palladium oxide. The catalyst may contain other oxides unless they deteriorate the activity and the life of the catalyst.

The proportions of the respective components, taking the total weight of the catalyst as 100%, are copper oxide 20–60 weight % (preferably 30–50 weight %), zinc oxide 10–50 weight % (preferably 20–40 weight %), aluminum oxide 2–10 weight % (preferably 4–8 weight %), silicon oxide 0.3–0.9 weight %, zirconium oxide 0–40 weight % (preferably 10–20 weight %), gallium oxide 0–10 weight % (preferably 0.1–5 weight %), and palladium oxide 0–10 weight % (preferably 0.1–5 weight %). By selecting the optimum composition for the intended reaction within the above quantitative ranges for components, a catalyst performance suitable for the reaction can be obtained.

Particular attention should be paid to the amount of silicon oxide although its content is very small. If the proportion of silicon oxide is smaller than the above-defined range, the catalyst life (retention of catalyst activity) will be insufficient. If the above range is exceeded, not only the catalyst activity but, in particular, the catalyst life will not be adequate. Thus, the superior effect of the invention is expressed only when the silicon oxide content is within the above range.

In addition, it is also important that the silicon oxide be derived from colloidal silica or dissolved silica in water. Colloidal silica and dissolved silica in water may be used in combination. When the catalyst is prepared using sodium silicate (water glass) or potassium silica, though both, too, are silicon compounds, for instance, a catalyst with the desired performance characteristics cannot be obtained.

When colloidal silica is used, it is preferable to use one with a sodium oxide content of less than 0.1 weight %, particularly not more than 0.06 weight %, i.e. substantially free of sodium. Incidentally, many of commercially available grades of colloidal silica contain about 0.2–0.6 weight % of sodium oxide.

When dissolved silica in water is employed, any of natural fresh water, tap water, well water, and industrial water can be used. Those waters contain about 20–100 ppm of dissolved silica. Dissolved silica is the silica assayable by molybdenum yellow or molybdenum blue absorptiometry (called calorimetric silica in the trade).

Furthermore, it is important that the copper-based catalyst of the present invention has been calcined at 480–690° C. With a calcination temperature below 480° C., the catalyst activity will be inadequate and the catalyst life will also not be sufficiently long. A calcination temperature over 690° C. also reduce catalyst activity and life. From the standpoint of catalyst performance, the calcination temperature should be selected from the range of 480–690° C. and particularly a comparatively high temperature between 520° C. and 680° C. is preferred. The particularly preferred calcination temperature is as high as 560–670° C.

Production of the Catalyst

The above catalyst is produced by a process which comprises mixing a solution A, which is an aqueous solution containing water-soluble salts of said metal components exclusive of the silicon component, with a solution B, which is an aqueous solution of a basic substance, to form a precipitate, aging the system when necessary, washing the precipitate, causing colloidal silica or silica dissolved in water to be adsorbed on the precipitate in the stage of said formation, aging, or washing of the precipitate, drying the washed precipitate, and calcining the same at 480–690° C. to thereby provide a calcined catalyst.

The above-mentioned mixing of solution A with solution B to provide a precipitate can be effected by mixing the two solutions directly to cause precipitation or, as an alternative, by providing, as solution A, an aqueous solution of one or more of the necessary metal components and an aqueous solution of the remaining metal components, mixing the first-mentioned aqueous solution with a basic aqueous solution containing a basic substance to precipitate the metal components contained in the first-mentioned solution and adding said aqueous solution of the remaining metal components to the solution containing the precipitate thus formed to cause precipitation of said remaining metal components. The allowable mode of mixing includes many other variations.

As the water-soluble salts of the metals other than silicon among the above-mentioned metal components, the nitrates and nitrites, which are highly water-soluble, can be used with advantage. As the basic substance mentioned above, any of sodium carbonate, potassium carbonate, sodium hydroxide, potassium hydroxide, and other bases can be used advantageously. In certain instances, ammonia, alkanolamines and other amines may also be employed.

Following precipitation, the precipitate is aged when necessary and, then, the precipitate is washed. Then, aftertreatments such as formation of a slurry and drying are carried out. An exemplary procedure following precipitation and aging comprises centrifugation or filtration, washing, formation of a slurry, and spray drying.

In the present invention, colloidal silica or dissolved silica in water is caused to be adsorbed on the precipitate in the step of precipitation, aging, or washing. Adsorption of colloidal silica on the precipitate in the precipitation step can be achieved by adding colloidal silica to either solution A or solution B or both or mixing solution A with solution B in the presence of water containing colloidal silica. In view of the finding that practically none of colloidal silica finds its way into the supernatant of the precipitation step or of the aging step and the finding that practically none of silica is eluted in the washing step after adsorption of colloidal silica, it is seen that the colloidal silica is not simply mixed with the precipitate but is adsorbed on the precipitate. Adsorption of dissolved silica in water can be achieved by preparing an aqueous solution of water-soluble salts of the component metals or an aqueous solution of a basic substance using water containing dissolved silica or washing the precipitate with water containing dissolved silica.

The precipitate on which colloidal silica has thus been adsorbed is calcined at a temperature of 480–690° C. (preferably 520–680° C., more preferably 560–670° C.) to provide a calcined catalyst. Calcination is carried out in an oxygen-containing atmosphere (usually air), whereby said metal components are converted to the corresponding oxides.

The catalyst thus obtained can be used as it is, or alternatively used as granulated or compression-molded by a suitable method beforehand. The particle diameter and morphology of the catalyst can be freely selected according to the reaction process and reactor geometry.

Reaction

The above catalyst is useful for the synthesis of methanol from hydrogen and carbon oxides or the reverse reaction thereof.

In applying the above catalyst to the reaction, the catalyst can be added as it is but it is common practice to reduce the catalyst with a reducing gas such as $H_2$ gas or $H_2$—$N_2$ mixture gas prior to use.

In methanol synthesis, a feed gas composed of hydrogen gas and carbon oxides ($CO_2$ alone or a mixture of $CO_2$ and CO gases) are caused to interact on the catalyst. This reaction is typically carried out at a reaction temperature of 150–300° C. and a reaction pressure of 1–10 MPa. In the reverse reaction, methanol is decomposed into hydrogen and carbon oxide. This reverse reaction is typically carried out at a reaction temperature of 200–400° C. and a reaction pressure of atmospheric pressure 1 MPa. Those reactions can be carried out in gaseous phase or in liquid phase. The solvent that can be used for the reaction in liquid phase includes hydrocarbons and other solvents which are insoluble or only sparingly soluble in water.

Effect

The copper-based catalyst according to the present invention comprises a structure comprising copper oxide, zinc oxide, and aluminum oxide as essential components (plus zirconium oxide, gallium oxide and palladium oxide as optional components), with colloidal silica or dissolved silica having been interposed in the structure in a defined proportion of 0.3–0.9 weight % as silicon oxide, which catalyst has been calcined at a specified high temperature within the range of 480–690° C.

Having the structure described above, the catalyst has an enhanced activity and a long life. This is probably because, in the catalyst, the silicon component prevents migration of the metal components. The activity-sustaining effect of the above structure is quite remarkable and the activity and life of this catalyst are outstanding as compared with any copper-based multicomponent catalyst so far proposed for methanol synthesis.

The present inventors' investigations revealed that the silicon oxide derived from colloidal silica or dissolved silica in water inhibits crystallization of metal oxides in the catalyst. For example, X-ray diffraction analysis of a copper oxide/zinc oxide/aluminum oxide/zirconium oxide catalyst after many hours of use in methanol synthesis revealed appreciable growth of Cu (reduced form), zinc oxide, and zirconium oxide crystals. On the other hand, when a copper oxide/zinc oxide/aluminum oxide/zirconium oxide catalyst containing a small amount of silica was used in methanol synthesis for many hours and, then, examined by X-ray diffraction analysis, it was found that the crystals of Cu (reduced form), zinc oxide, and zirconium oxide had not grown in any appreciable measure. Thus, the effect of inclusion of silicon oxide in a small proportion is inhibition of the growth of crystals of various components in the catalyst to help maintain a high degree of dispersion for a long time.

EXAMPLES

The following examples illustrate the present invention in further detail, it being to be understood, however, that the invention is by no means limited to the specific examples.

Production of the Catalyst

Example 1

Copper nitrate $3H_2O$ (54.3 g), zinc nitrate $6H_2O$ (39.1 g), aluminum nitrate $9H_2O$ (6.6 g), zirconium nitrite $2H_2O$ (15.4 g), and colloidal silica [Snowtex ST-O, Nissan Chemical Industries] (1.26 g) were dissolved in distilled water to make 500 ml. This solution was used as solution A. Snowtex ST-O, mentioned above, is a clear milk-white slurry with a silicic anhydride ($SiO_2$) content of 20–21 wt. %, a sodium oxide ($Na_2O$) content of not more than 0.04 wt. %, pH 2–4, particle diameter 10–20 μm, viscosity not higher than 3 cps/25° C., specific gravity 1.12–1.14/25° C., and freeze point 0° C.

Separately, sodium carbonate $10H_2O$ (139.0 g) was dissolved in distilled water to make 500 ml. This aqueous solution was used as solution B.

Solutions A and B were concurrently added dropwise into 400 ml of distilled water under vigorous stirring at a rate of 10 ml/min. for both (this procedure is called coprecipitation). The mixture was allowed to stand for 24 hours and the resulting precipitate was washed with distilled water, dried at 110° C., and calcined in air at 600° C. for 2 hours to provide the objective catalyst.

The composition of this catalyst was CuO: 45.2 wt. % ZnO: 27.1 wt. %, $Al_2O_3$: 4.5 wt. %, $ZrO_2$: 22.6 wt. %, $SiO_2$: 0.6 wt. %.

Example 2

Copper nitrate $3H_2O$ (67.8 g), zinc nitrate $6H_2O$ (52.2 g), aluminum nitrate $9H_2O$ (13.1 g), and colloidal silica (Snowtex ST-O, Nissan Chemical Industries) (0.86 g) were dissolved in distilled water to make 500 ml. This aqueous solution was used as solution A.

Separately, sodium carbonate $10H_2O$ (160.0 g) was dissolved in distilled water to make 500 ml. This aqueous solution was used as solution B.

A catalyst was produced under the same conditions as in Example 1. The composition of this catalyst was CuO: 55.4 wt. %, ZnO: 35.4 wt. %, $Al_2O_3$: 8.8 wt. %, $SiO_2$: 0.4 wt. %.

Example 3

Copper nitrate $3H_2O$ (54.3 g), zinc nitrate $6H_2O$ (39.1 g), aluminum nitrate $9H_2O$ (6.6 g), and zirconium nitrite $2H_2O$ (15.4 g) were dissolved in distilled water to make 500 ml. This aqueous solution was used as solution A.

Separately, sodium carbonate $10H_2O$ (139.0 g) was dissolved in distilled water to make 500 ml. This aqueous solution was used as solution B.

Solutions A and B were concurrently added dropwise into 400 ml of distilled water under vigorous stirring at a rate of 10 ml/min. for both. The mixture was allowed to stand for 24 hours and the resulting precipitate was washed 3 times with 4 liters of distilled water con taining 0.4 g of colloidal silica (Snowtex ST-O, Nissan Chemical Industries). The washed precipitate was dried at 110° C. and calcined in air at 600° C. for 2 hours to provide the objective catalyst.

The composition of this catalyst was CuO: 45.2 wt. %, ZnO: 27.1 wt. %, $Al_2O_3$: 4.5 wt. %, $ZrO_2$: 22.6 wt. %, $SiO_2$: 0.6 wt. %.

Example 4

Copper nitrate $3H_2O$ (54.3 g), zinc nitrate $6H_2O$ (39.1 g), aluminum nitrate $9H_2O$ (6.6 g), zirconium nitrite $2H_2O$ (14.1 g), and gallium nitrate $6H_2O$ (1.4 g) were dissolved in a sufficient amount of water containing 45 ppm of dissolved silica (hereinafter referred to as silica-dissolved water) to make 500 ml. This aqueous solution was used as solution A.

Separately, sodium carbonate $10H_2O$ (139.0 g) was dissolved in silica-dissolved water to make 500 ml. This aqueous solution was used as solution B.

Solutions A and B were concurrently added dropwise into 400 ml of silica-dissolved water under vigorous agitation at a rate of 10 ml/min for both and the mixture was aged for 24 hours. The resulting precipitate was washed 3 times with 3 liters of silica-dissolved water and then processed into a catalyst as in Example 1 (drying at 110° C. and calcination in air at 600° C.).

The oxide composition of the above catalyst was CuO: 45.2 wt. %, ZnO: 27.1 wt. %, $Al_2O_3$: 4.5 wt. %, $ZrO_2$: 20.8 wt. %, $Ga_2O_3$: 1.8 wt. %, $SiO_2$: 0.6 wt. %.

Comparative Example 1

Copper nitrate $3H_2O$ (54.3 g), zinc nitrate $6H_2O$ (39.1 g), aluminum nitrate $9H_2O$ (6.6 g), and zirconium nitrate $2H_2O$ (15.4 g) were dissolved in distilled water to make 500 ml. This aqueous solution was used as solution A.

Separately, sodium carbonate $10H_2O$ (139.0 g) was dissolved in distilled water to make 500 ml. This aqueous solution was used as solution B.

The procedure of Example 1 was otherwise followed to prepare a catalyst. The composition of this catalyst was CuO: 45.5 wt. %, ZnO: 27.3 wt. %, $Al_2O_3$: 4.5 wt. %, $ZrO_2$: 22.7 wt. %.

Comparative Example 2

Copper nitrate $3H_2O$ (54.3 g), zinc nitrate $6H_2O$ (39.1 g), aluminum nitrate $9H_2O$ (6.6 g), zirconium nitrite $2H_2O$ (15.4 g), and colloidal silica (Snowtex ST-O, Nissan Chemical Industries) (3.8 g) were dissolved in distilled water to make 500 ml. This aqueous solution was used as solution A.

Separately, sodium carbonate $10H_2O$ (139.0 g) was dissolved in distilled water to make 500 ml. This aqueous solution was used as solution B.

The procedure of Example 1 was otherwise repeated to prepare a catalyst. The composition of this catalyst was CuO: 44.6 wt. %, ZnO: 26.7 wt. %, $Al_2O_3$: 4.5 wt. %, $ZrO_2$: 22.3 wt. %, $SiO_2$: 1.9 wt. %.

Comparative Example 3

Copper nitrate $3H_2O$ (54.3 g), zinc nitrate $6H_2O$ (39.1 g), aluminum nitrate $9H_2O$ (6.6 g), and zirconium nitrite $2H_2O$ (15.4 g) were dissolved in distilled water to make 500 ml. This aqueous solution was used as solution A.

Separately, sodium carbonate $10H_2O$ (139.0 g) was dissolved in distilled water to make 500 ml. This aqueous solution was used as solution B.

To 400 ml of distilled water was added 1.9 g of colloidal silica (Snowtex ST-O) and while this aqueous solution was vigorously stirred, the above solutions A and B were concurrently added dropwise at a rate of 10 ml/min. for both. The resulting precipitate was washed with distilled water, dried at 110° C., and calcined in air at 600° C. for 2 hours to provide the objective catalyst.

The composition of this catalyst was CuO: 45.0 wt. %, ZnO: 27.0 wt. %, $Al_2O_3$: 4.5 wt. %, ZrO.: 22.4 wt. %, $SiO_2$: 1.1 wt. %.

Comparative Examples 4–5 and Example 5

Using the following calcining conditions, the procedure of Example 1 was otherwise repeated to prepare catalysts. Regardless of the conditions of calcination, the catalysts were identical with the catalyst of Example 1 in composition.

Comparative Example 4

Calcination temperature: 350° C., calcination time: 2 hr.

Comparative Example 5

Calcination temperature: 700° C., calcination time: 2 hr.

Example 5

Calcination temperature: 500° C., calcination time: 2 hr.

Comparative Example 6

Copper nitrate $3H_2O$ (67.8 g), zinc nitrate $6H_2O$ (65.2 g), and colloidal silica (Snowtex ST-O) (0.76 g) were dissolved in distilled water to make 500 ml. This aqueous solution was used as solution A.

Separately, sodium carbonate $10H_2O$ (157.4 g) was dissolved in distilled water to make 500 ml. This aqueous solution was used as solution B.

A catalyst was prepared under the same conditions as in Example 1. The composition of this catalyst was CuO: 55.4 wt. %, ZnO: 44.2 wt. %, $SiO_2$: 0.4 wt. %.

Comparative Example 7

Copper nitrate $3H_2O$ (54.3 g), zinc nitrate $6H_2O$ (39.1 g), aluminum nitrate $9H_2O$ (6.6 g), and zirconium nitrite $2H_2O$ (15.4 g) were dissolved in distilled water to make 500 ml. This aqueous solution was used as solution A.

Separately, sodium carbonate $10H_2O$ (139.0 g) and sodium silicate solution ($SiO_2$ content 55 wt. %) (0.4 g) were dissolved in distilled water to make 500 ml. This aqueous solution was used as solution B.

A catalyst was prepared under otherwise the same conditions as in Example 1. The composition of this catalyst was CuO: 45.2 wt. %, ZnO: 27.1 wt. %, $Al_2O_3$: 4.5 wt. %, $ZrO_2$: 22.6 wt. %, $SiO_2$: 0.6 wt. %

Summary of Catalyst Composition and Production Conditions

For assisting in understanding, the oxide compositions of the above catalysts and the production conditions are summarized in Table 1. In the column "Method of addition of Si", (a) represents the case in which colloidal silica for the Si component was added to an aqueous solution of metal salts (solution A), (b) represents the case in which colloidal silica for the Si component was added to the water used for washing the precipitate, (c) represents the case in which all the procedures for preparing solutions A and B, mixing the two solutions, and washing the precipitate were carried out using silica-dissolved water, (d) represents the case in which an aqueous solution of metal salts (solution A) and an aqueous solution of a base (solution B) were added to the water containing colloidal silica for the Si component, and (e) represents the case in which sodium silicate for the Si component was added to an aqueous solution of a base (solution B).

TABLE 1

| | Oxide composition of catalyst | | | | | | Calcination temperature (° C.) | Method of addition of Si |
|---|---|---|---|---|---|---|---|---|
| | CuO | ZnO | $Al_2O_3$ | $ZrO_2$ | $Ga_2O_3$ | $SiO_2$ | | |
| Ex. 1 | 45.2 | 27.1 | 4.5 | 22.6 | — | 0.6 | 600 | (a) |
| Ex. 2 | 55.4 | 35.4 | 8.8 | — | — | 0.4 | 600 | (a) |
| Ex. 3 | 45.2 | 27.1 | 4.5 | 22.6 | — | 0.6 | 600 | (b) |
| Ex. 4 | 45.2 | 27.1 | 4.5 | 20.8 | 1.8 | 0.6 | 600 | (c) |
| Ex. 5 | 45.2 | 27.1 | 4.5 | 22.6 | — | 0.6 | 500 | (a) |

TABLE 1-continued

| | Oxide composition of catalyst | | | | | | Calcination temperature (° C.) | Method of addition of Si |
|---|---|---|---|---|---|---|---|---|
| | CuO | ZnO | Al$_2$O$_3$ | ZrO$_2$ | Ga$_2$O$_3$ | SiO$_2$ | | |
| Com. Ex. 1 | 45.5 | 27.3 | 4.5 | 22.7 | — | — | 600 | — |
| Com. Ex. 2 | 44.6 | 26.7 | 4.5 | 22.3 | — | 1.9 | 600 | (a) |
| Com. Ex. 3 | 45.0 | 27.0 | 4.5 | 22.4 | — | 1.1 | 600 | (d) |
| Com. Ex. 4 | 45.2 | 27.1 | 4.5 | 22.6 | — | 0.6 | 350 | (a) |
| Com. Ex. 5 | 45.2 | 27.1 | 4.5 | 22.6 | — | 0.6 | 700 | (a) |
| Com. Ex. 6 | 55.4 | 44.2 | — | — | — | 0.4 | 600 | (a) |
| Com. Ex. 7 | 45.2 | 27.1 | 4.5 | 22.6 | — | 0.6 | 600 | (e) |

(Ex. and Com. Ex. represent Example and Comparative Example, respectively.)

Catalyst Activity Test for Methanol Synthesis

A tubular reactor was packed with 2 ml of the catalyst which was then reduced by passing a reducing gas composed of 10 vol. % of H$_2$ and 90 vol. % of N$_2$, preheated to a temperature of 300° C., for 2 hours. After this reduction of the catalyst, a mixture gas composed of 22 vol. % of CO$_2$, 3 vol. % of CO, and 75 vol. % of H$_2$ was passed through the catalyst bed at a flow rate of 20 L/hr. to conduct the reaction at a pressure of 5 MPa and a temperature of 250° C. The reaction product gas was serially analyzed by gas chromatography to study the relationship between time on stream and methanol yield.

Influence of Calcination Temperature

To investigate the influence of calcination temperature, the methanol synthesis reaction was carried out using the catalyst of Example 1 (calcined at 600° C. for 2 hr.), the catalyst of Example 5 (calcined at 500° C. for 2 hr.), the catalyst of Comparative Example 4 (calcined at 350° C. for 2 hr.), and the catalyst of Comparative Example 5 (calcined at 700° C. for 2 hr.), all of which were of the same oxide composition, respectively under the same conditions as above. The results are shown in FIG. 1.

Figure 1:
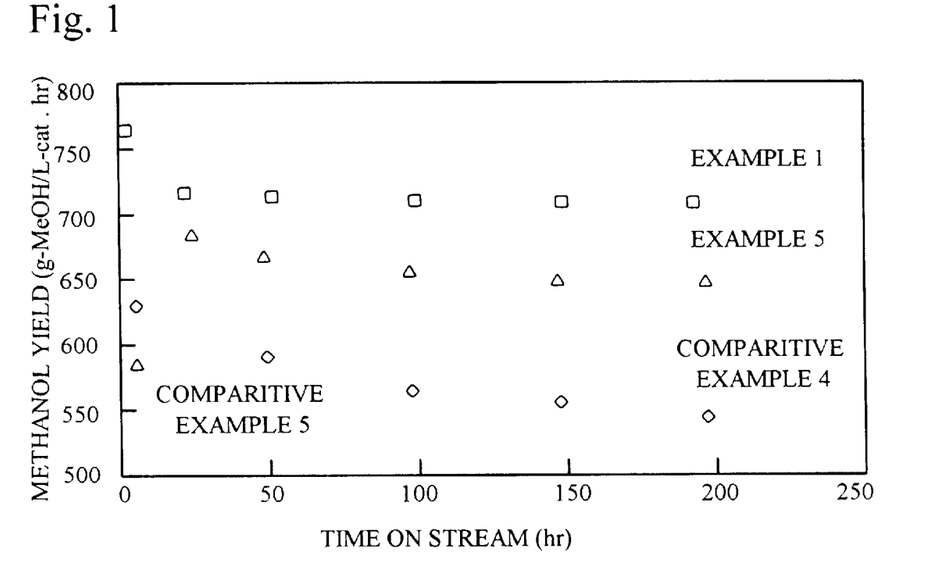
FIG. 1 is a diagrammatic representation of the relationship between time on stream and methanol yield in the reactions using the catalysts of Examples 1 and 5 and Comparative Examples 4 and 5, respectively (the influence of calcination temperature on the activity and the long-term stability of the catalyst)

As can be seen from FIG. 1, the catalyst calcined at 600° C. gave the best result (the yield of methanol was 740 g MeOH/L Cat·hr. in the initial phase of reaction and 740 g MeOH/L Cat·hr. even after 200 hr.), seconded by the catalyst calcined at 500° C. (the yield of methanol after 200 hr. was 650 g MeOH/L Cat·hr.). The catalyst calcined at 350° C. was obviously inferior (the yield of methanol was 630 g MeOH/L Cat·hr. in the initial phase of reaction and 545 g MeOHIL Cat·hr. after 200 hr.) and the catalyst calcined at 700° C. was also inferior in terms of initial activity (585 g MeOH/L Cat·hr. in the initial phase of reaction).

It is apparent that the most favorable result was obtained with the calcination temperature of 600° C., with 500° C. resulting in the second best result, that when the calcination temperature was as low as 350° C., the yield of methanol was low and the catalyst activity decreased considerably with time on stream, and that when the calcination temperature was as high as 700° C., the yield of methanol was considerably decreased. Though not represented in FIG. 1, a detailed experiment performed using the same catalyst composition as in Example 1 but varying the calcination temperature in more delicate steps showed that the calcination temperature should be 480–690° C., preferably 520–680° C., and more preferably 560–670° C.

Influence of the Amount of Adsorption of Colloidal Silica

Figure 2:
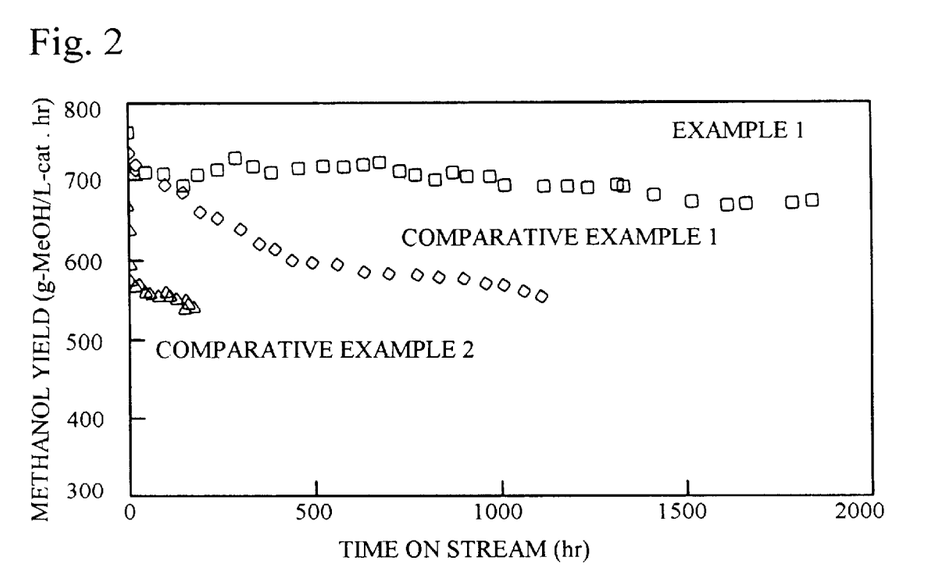
FIG. 2 is a diagrammatic representation of the relationship between time on stream and methanol yield in the reactions using the catalysts of Example 1 and Comparative Examples 1 and 2, respectively (the influence of the amount of adsorption of colloidal silica on the activity and the long-term stability of the catalyst)

FIG. 2 is a diagrammatic representation of the relationship between time on stream (hr.) and the yield of methanol (g MeOH/L Cat·hr.) in the reaction carried out using each of the catalyst of Example 1 and the catalysts of Comparative Examples 1 and 2. Since it was confirmed from the data plotted in FIG. 1 that, when colloidal silica was caused to be adsorbed (SiO$_2$ content 0.6 weight %), the preferred calcination temperature was 600° C. for the composition of Example 1, a further experiment was carried out using substantially the same metal oxide composition and the same calcination temperature of 600° C. for comparing the case in which SiO$_2$ was not added (Comparative Example 1) with the case in which the SiO$_2$ content was increased to 1.9 weight % (Comparative Example 2). It can be seen from FIG. 2 that there is an optimum value for SiO$_2$ content as well.

Figure 3:
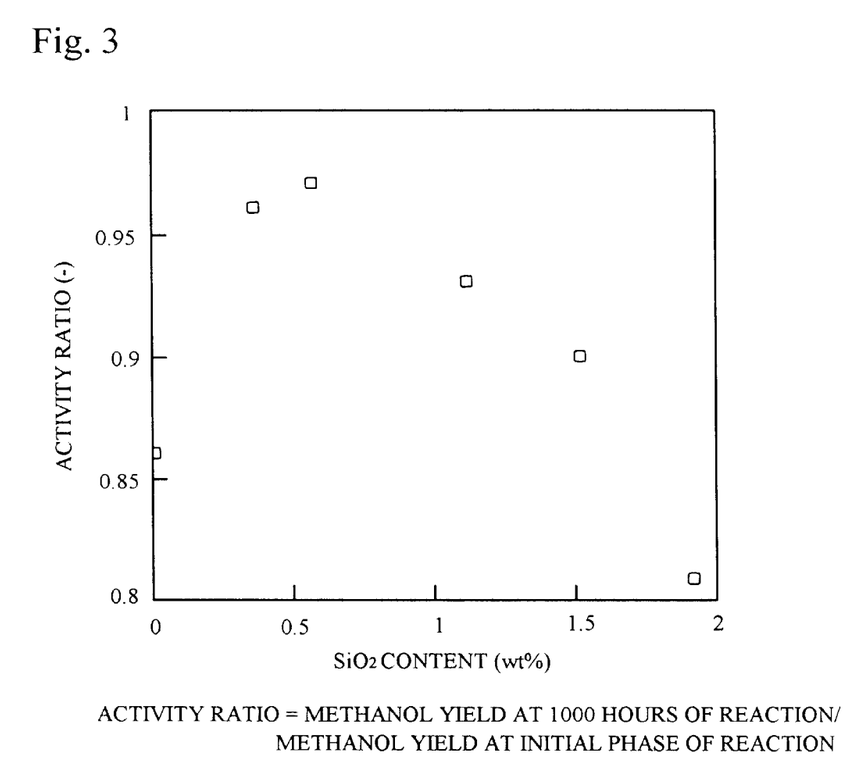
FIG. 3 is a diagrammatic representation of the relationship between colloidal silica-derived $SiO_2$ content and activity ratio (methanol yield at 1000 hours of reaction/methanol yield at initial phase of reaction)

In order to scrutinize the influence of SiO$_2$ derived from colloidal silica, the relationship between SiO$_2$ content and activity ratio (methanol yield after 1000 hr./methanol yield in the initial phase of reaction) was studied by using the oxide composition of Example 1 and varying the SiO$_2$ content. The results are plotted in FIG. 3. Thus, FIG. 3 shows the results of Comparative Examples 1–3, together with the results of Example 2, which is somewhat different in oxide composition, however, and of an additional example in which an SiO$_2$ content of 1.5 weight % was used. It can be seen from FIG. 3 that when the oxide composition was identical or similar to the composition of Example 1, SiO$_2$ in too large amount or in too small amount invariably exerted an unfavorable influence, that satisfactory results were obtained when the SiO$_2$ content was 0.3–0.9 weight %, and that the optimum result was obtained when the SiO$_2$ content was approximately 0.6 weight %.

Comparison of Colloidal Silica with Sodium Silicate

Figure 4:
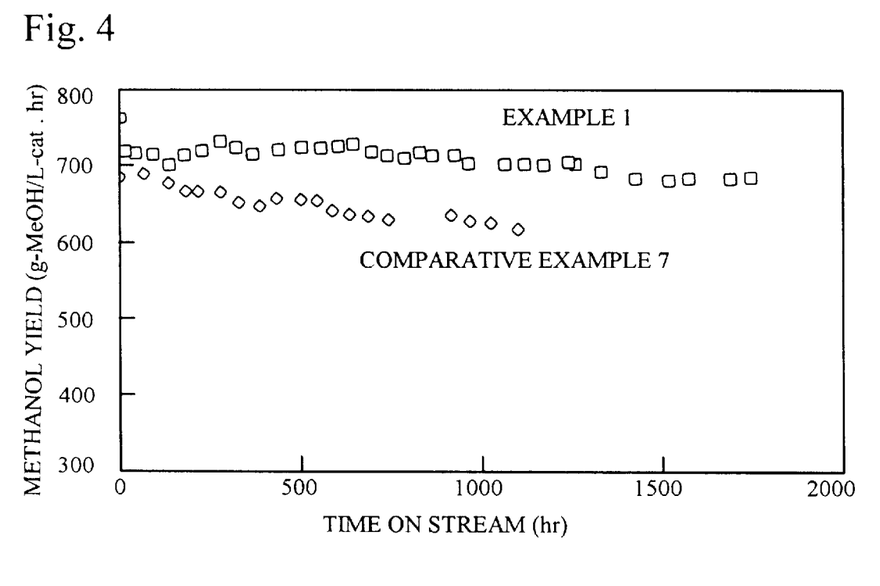
FIG. 4 is a diagrammatic representation of the relationship between time on stream and methanol yield in the reactions using the catalyst of Example 1 and the catalyst of Comparative Example 7 (the influence of the kind of $SiO_2$ source on the activity and the long-term stability of the catalyst)

As it was clear from the results plotted in FIGS. 2 and 3 that the optimum result could be obtained when the amount of SiO$_2$ derived from colloidal silica was 0.6 weight % (Example 1, calcination temperature 600° C.), a comparative experiment was carried out using sodium silicate instead of colloidal silica (Comparative Example 7, calcination temperature 600° C., SiO$_2$ content 0.6 wt. %). The results are shown in FIG. 4. It is clear from FIG. 4 that the use of colloidal silica as the source of SiO$_2$ resulted in a superior performance in both catalyst activity and life.

Influence of Oxide Composition

Figure 5:
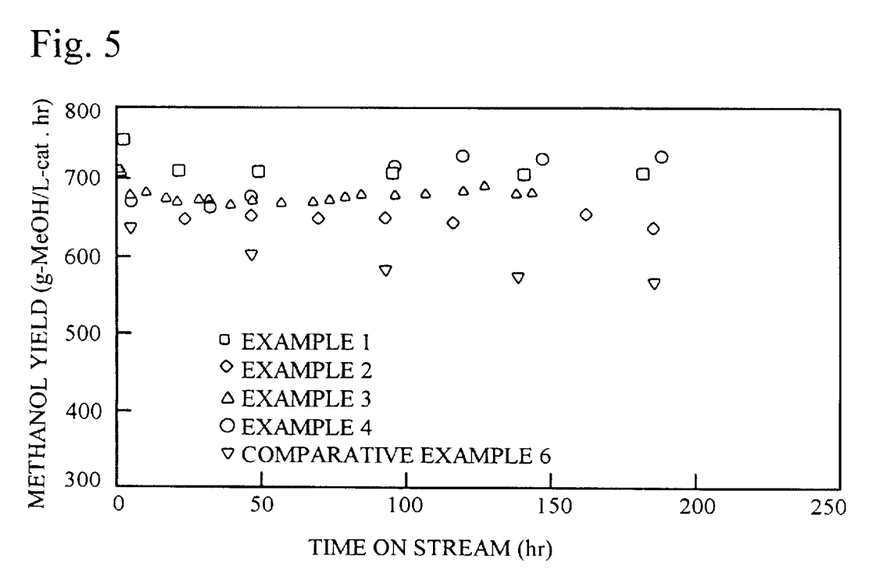
FIG. 5 is a diagrammatic representation of the relationship between time on stream and methanol yield as found with the catalysts of Examples 1–4 and the catalyst of Comparative Example 6 (the influence of oxide composition on the activity and the long-term stability of the catalyst).

The relationship between time on stream and methanol yield is shown in FIG. 5 for each of the catalysts of Examples 1–4 and the catalyst of Comparative Example 6. It is clear from FIG. 5 that the CuO/ZnO/Al$_2$O$_3$/SiO$_2$/ZrO$_2$ catalysts of Examples 1 and 3 are superior to the ZrO$_2$-free CuO/ZnO/Al$_2$O$_3$/SiO$_2$ catalyst of Example 2 and that the CuO/ZnO/Al$_2$O$_3$/SiO$_2$/ZrO$_2$/Ga$_2$O$_3$ catalyst of Example 4, which further contains Ga$_2$O$_3$, is also as satisfactory. In contrast, the Al$_2$O$_3$-free CuO/ZnO/SiO$_2$ series catalyst according to Comparative Example 6 did not show a remarkable decrease in activity with time but was considerably inferior in terms of the absolute yield of methanol. The variation in results due to different methods of addition of colloidal silica was not remarkable.

Production of Palladium-containing Oxide Catalysts and a Catalyst Life Test

Example 6

Copper nitrate 3H$_2$O (30.8 g), zinc nitrate 6H$_2$O (27.8 g), aluminum nitrate 9H$_2$O (9.1 g), zirconium nitrite 2H$_2$O (12.8 g), 10% aqueous palladium nitrate solution (0.5 g), and colloidal silica (Snowtex ST-O, Nissan Chemical Industries) (0.60 g) were dissolved in distilled water to make 250 ml and this aqueous solution was used as solution A.

Separately, sodium carbonate $10H_2O$ (78.0 g) was dissolved in distilled water to make 250 ml and this aqueous solution was used as solution B.

A catalyst was prepared under otherwise the same conditions as in Example 1. The composition of this catalyst was CuO: 39.6 wt. %, ZnO: 29.7 wt. %, $Al_2O_3$: 5.0 wt. %, $ZrO_2$: 22.8 wt. %, PdO: 2.3 wt. %, $SiO_2$: 0.6 wt. %.

A tubular reactor was packed with 2 ml of the above catalyst which was then reduced with a reducing gas composed of 10 vol. % of $H_2$ and 90 vol. % of $N_2$ preheated to 300° C. for 2 hours. After this reduction of the catalyst, a mixture gas composed of 22 vol. % of $CO_2$, 3 vol. % of CO, and 75 vol. % of $H_2$ was fed through the catalyst bed at a flow rate of 20 L/hr to carry out a methanol synthesis reaction at a pressure of 5 MPa and a temperature of 250° C. The product gas was serially analyzed by gas chromatography and the relationship between time on stream and methanol yield was investigated.

The methanol yield was 682 g MeOH/L Cat·hr. after 5 hr. of reaction and 674 g MeOH/L Cat·hr. after 200 hr. of reaction and the activity ratio (methanol yield at 200 hr. of reaction/methanol yield at 5 hr. of reaction) was 98.8%.

Comparative Example 8

Except that colloidal silica was not used, the procedure of Example 6 was repeated to provide a catalyst. The composition of this catalyst was CuO: 39.8 wt. %, ZnO: 29.9 wt. %, $Al_2O_3$: 5.0 wt. %, $ZrO_2$: 23.0 wt. %, PdO: 2.3 wt. %.

The yield of methanol in the reaction carried out under the same conditions as in Example 6 was 690 g MeOH/L Cat·hr. at 5 hr. of reaction and 641 g MeOH/L Cat·hr. at 200 hr. and the activity ratio (methanol yield at 200 hr. of reaction/methanol yield at 5 hr. of reaction) was 92.9%.

Catalyst Activity Test in the Decomposition Reaction of Methanol

A reactor tube was packed with 2 ml of the catalyst obtained in Example 1, which was then reduced by passing a reducing gas composed of 10 vol. % of $H_2$ and 90 vol. % of $N_2$ preheated to 300° C. for 2 hours. After this reduction of the catalyst, a 1:1 (by mole) mixture of methanol and $N_2$ gases was passed through the catalyst bed at a flow rate of 10 L/hr. to carry out the decomposition reaction at a pressure of 0.5 MPa and a temperature of 300° C. The decomposition rate of methanol was 99.9%, the selectivity for $H_2$ and CO was 99.5%, and the exit gas composition ratio $H_2/CO$ was 2.0/1.

It is clear from the above detailed description that the copper-based catalyst of the invention has a high catalyst activity and a long catalyst life providing sustained activity for long term. Both the catalyst activity and catalyst life achieved by the invention are remarkably high as compared with any of the hitherto-proposed copper-based multicomponent catalysts for methanol synthesis. The present invention, therefore, is of great industrial value.

What is claimed is:

1. A copper-based catalyst essentially comprising copper oxide, zinc oxide, aluminum oxide, and silicon oxide, optionally together with zirconium oxide, gallium oxide, and palladium oxide, wherein with the total weight of the catalyst being taken as 100%, said oxides account for, in the order mentioned, 20–60 weight %, 10–50 weight %, 2–10 weight %, 0.3–0.9 weight %, 0–40 weight %, 0–10 weight %, and 0–10 weight %, respectively, and said silicon oxide has been derived from colloidal silica or dissolved silica in water, which catalyst has been subjected to calcination at 520–680° C.

2. The copper-based catalyst according to claim 1 which is a catalyst for methanol synthesis from hydrogen and carbon oxides or the reverse reaction thereof.

3. A method of producing a copper-based catalyst essentially comprising copper oxide, zinc oxide, aluminum oxide, and silicon oxide, optionally together with zirconium oxide, gallium oxide, and palladium oxide, wherein with the total weight of the catalyst being taken as 100%, said oxides account for, in the order mentioned, 20–60 weight %, 10–50 weight %, 2–10 weight %, 0.3–0.9 weight %, 0–40 weight %, 0–10 weight %, and 0–10 weight %, respectively, which comprises mixing a solution A, which is an aqueous solution containing water-soluble salts of said metal components exclusive of the silicon component, with a solution B, which is an aqueous solution of a base, to form a precipitate, aging the mixture where necessary, washing the precipitate with water, causing colloidal silica or silica dissolved in water to be adsorbed on the precipitate in the step of said formation, aging, or washing of the precipitate, drying the washed precipitate, and calcining the same at 520–680° C. to provide a calcined catalyst.

* * * * *